United States Patent
Liu et al.

(10) Patent No.: US 10,669,532 B2
(45) Date of Patent: Jun. 2, 2020

(54) **RECOMBINANT STRAIN OF *BACILLUS SUBTILIS***

(71) Applicant: JIANGNAN UNIVERSITY, Wuxi (CN)

(72) Inventors: Long Liu, Wuxi (CN); Yang Gu, Wuxi (CN); Jieying Deng, Wuxi (CN); Jian Chen, Wuxi (CN); Guocheng Du, Wuxi (CN); Jianghua Li, Wuxi (CN)

(73) Assignee: JIANGNAN UNIVERSITY, Suzhou (CN)

( * ) Notice: Subject to any disclaimer, the term of this patent is extended or adjusted under 35 U.S.C. 154(b) by 0 days.

(21) Appl. No.: 16/052,566

(22) Filed: Aug. 1, 2018

(65) Prior Publication Data

US 2020/0032237 A1   Jan. 30, 2020

(30) Foreign Application Priority Data

Jul. 24, 2018   (CN) .......................... 2018 1 0818899

(51) Int. Cl.
| | |
|---|---|
| *C12N 1/21* | (2006.01) |
| *C12N 9/04* | (2006.01) |
| *C12N 9/02* | (2006.01) |
| *C12N 9/88* | (2006.01) |
| *C12N 9/00* | (2006.01) |
| *C12P 19/02* | (2006.01) |
| *C12P 19/28* | (2006.01) |

(52) U.S. Cl.
CPC ............ *C12N 9/93* (2013.01); *C12N 9/0006* (2013.01); *C12N 9/0008* (2013.01); *C12N 9/0095* (2013.01); *C12P 19/02* (2013.01); *C12Y 101/01042* (2013.01); *C12Y 101/05004* (2013.01); *C12Y 102/07001* (2013.01); *C12Y 102/07006* (2013.01); *C12Y 118/06001* (2013.01); *C12Y 604/01001* (2013.01)

(58) Field of Classification Search
None
See application file for complete search history.

(56) References Cited

FOREIGN PATENT DOCUMENTS

CN   106148261 A   * 11/2016

OTHER PUBLICATIONS

Integration. (1992). In C. G. Morris (Ed.), Academic Press Dictionary of Science and Technology (4th ed.). Oxford, UK: Elsevier Science & Technology. Retrieved from search.credoreference.com/content/entry/apdst/integration/0?institutionId=743.*

Liu et al. ("Pathway engineering of Bacillus subtilis for microbial production of N-acetylglucosamine," Metabolic Eng., 2013, 19, 107-15.*

Jasniewski et al., The Fe protein: an unsung hero of nitrogenase, Inorganics, 2018, 6, 25.*

Mortenson, Structure and function of nitrogenase, Ann. Rev. Biochem., 1979, 48, 387-41.*

Gu et al., Synthetic redesign of central carbon and redox metabolism for high yield production of N-acetylglucosamine in Bacillus subtilis, Metabolic Eng., 2019, 51, 59-69.*

* cited by examiner

*Primary Examiner* — Robert B Mondesi
*Assistant Examiner* — Todd M Epstein
(74) *Attorney, Agent, or Firm* — SZDC Law P.C.

(57) ABSTRACT

The invention relates to a recombinant strain of *Bacillus subtilis*, wherein pyruvate carboxylase BalpycA, glyceraldehyde-3-phosphate ferredoxin dehydrogenase gor, isocitrate NAD$^+$ dehydrogenase icd, malate quinone dehydrogenase mqo, pyruvate ferredoxin oxidoreductase porAB and nitrogenase ferritin cyh are integrated and expressed in the recombinant strain. The invention also discloses use of the recombinant strain in fermentation production of acetylglucosamine. The recombinant *Bacillus subtilis* of the invention eliminates the central carbon metabolism overflow of the *Bacillus subtilis* and balances the intracellular reducing force, and the fermentation yield of acetylglucosamine is greatly improved.

2 Claims, 2 Drawing Sheets

Specification includes a Sequence Listing.

SEQUENCE LISTING

<160> NUMBER OF SEQ ID NOS: 12

<210> SEQ ID NO 1
<211> LENGTH: 1000
<212> TYPE: DNA
<213> ORGANISM: Artificial Sequence
<220> FEATURE:
<223> OTHER INFORMATION: upstream sequence of the integration malS locus

<400> SEQUENCE: 1

```
taaagacaga ctctgacagg agtctgtttt ttttatgggc cgtttgctac catgatgata      60
ggggggggtg aaaatggaaa caatgaaaat tggaaacatc acgttgacct ggcttgacgg     120
aggcgtgacg catatggacg gaggcgccat gttcggcgtt gtgccaaagc cgctttggtc     180
taaaaaatat ccagtcaatg aaaaaaacca gattgaacta agaacagacc ctattttgat     240
tcaaaaggat gggctcaata tcatcattga cgccggaatt gggtacggca agctgactga     300
taaacaaaaa cgaaactatg gcgtgacaca agagtcgaat gtgaaaccct cattagctgc     360
actcggatta acggttgccg atatagatgt gatcgcaatg acacaccttc attttgatca     420
tgcatgcggt ttaacggaat atgaaggtga acggctcgtc tctgtctttc cgaatgcagt     480
gatttataca tcagctgttg aatgggacga aatgcgccat ccgaatatca ggtcgaaaaa     540
tacgtattgg aaagaaaatt gggaggctgt agctggccaa gtcaaaacct ttgaagacac     600
cttaacgatc acagagggta ttacaatgca tcacaccgga ggccatagcg acggacacag     660
tgtcctgata tgcgaggatg cgggtgaaac tgccgtacat atggcagatc tgatgccgac     720
acatgcccac cgcaatccgc tatgggtgct ggcttacgat gattatccga tgacctctat     780
cccgcaaaag cagaaatggc aggcgttcgc agcagaaaaa gatgcttggt ttatttttta     840
ccatgatgcc gagtatcgcg cccttcaatg ggaggaggac ggaagcatca aaaagtcagt     900
```

```
taagcgaatg aagcgatagc atattttat gtttaccctg catgttttcc ggctaataat      960
gcaaacctag tactattatg ctcagaaagg aagaggcagg                          1000
```

<210> SEQ ID NO 2
<211> LENGTH: 1000
<212> TYPE: DNA
<213> ORGANISM: Artificial Sequence
<220> FEATURE:
<223> OTHER INFORMATION: Downstream sequence of malS locus

<400> SEQUENCE: 2

```
taaaaaagag ccgctgcata ggcagcggct tctattttt gcttgtccgg tgttaagagg      60
cgattgtatc aatgacatca acaatttctc ccgttttcgc atccaccatg acttcatact    120
gttctaattc tccgaaagct gatcgtgtaa tgccggtttt gtatacctgt accgtttctc    180
cgttaatatt gtagggctcc ggctgggtgt aaatccatga tccgtcaatc gggccccgct    240
gcttaaaagc agatttaca attcgaagcg ctttttctga agaaatataa ggcttcatca    300
catattgtct cacaacgaca gccgtacaaa ttccaagtcc tgctcctaaa agaagatgac    360
gcaatttcaa aataaagcac ctcctggttg atcgtacttt tcattataca gaaacagcca    420
aatcctgtta agcaatacgc ggctgatcga gcagattggg tcagagtgct tggaaaactt    480
cattgtttct aataaaataa aaggactaca tagaaatgag gggaaaacat gaatcaagaa    540
acgaaagcgc ttttccaaac actgacgcag cttcccggcg cgccgggcaa tgagcatcag    600
gttcgtgctt ttatgaagca ggagctagcc aaatatgcag atgacatcgt tcaggacaga    660
ctgggaagtg ttttcggagt cagacgaggc gcagaggacg caccgagaat tatggtagcc    720
gggcacatgg acgaagtcgg cttcatggtg acatccatta cagacaacgg gctgctcaga    780
ttccagacgc tcggaggctg gtggagccaa gttttgcttg cgcagcgggt tgaaattcaa    840
acagataacg ggccggttcc gggtgtgatt tcaagcatac cgccgcattt attgacagat    900
gcgcagcgaa accgaccgat ggatatcaaa aacatgatga tcgacattgg agcggatgat    960
aaggaagacg ccatcaaaat cggcattaga ccgggacagc                         1000
```

<210> SEQ ID NO 3
<211> LENGTH: 1000
<212> TYPE: DNA
<213> ORGANISM: Artificial Sequence
<220> FEATURE:
<223> OTHER INFORMATION: Upstream sequence of the integration pyk locus

<400> SEQUENCE: 3

```
gaaacgaata ggggtattaa cgagcggcgg ggattccccg ggaatgaacg cagcagttcg      60
cgcagtagtc agaaaagcga tctatcatga cgttgaagtt tacggtattt acaacgbata    120
cgcgggattg atcagcggaa agattgaaaa gcttgaactc ggatcagtag gcgatattat    180
acatcgtgga gggactaagc tttatacggc gagatgtcct gaattcaaaa cagttgaagg    240
ccgtgaaaaa gggatagcaa acttgaagaa gcttggtatt gaaggccttg ttgttatcgg    300
tggagacggt tcctatatgg gtgcgaaaaa attaacggaa cacgggtttc catgtgtagg    360
tgtaccgggt acaattgata tgacattcc ggcactgat tttacaatcg gtttcgatac    420
agctttaaat acagtaattg acgcaattga taagattcgc gatacagcga cttctcatga    480
acgtacatat gtaatcgaag taatgggccg tcatgccggc gatatcgcat tgtgggccgg    540
tcttgcaggg ggcgcagaat cgatcttaat ccctgaggca gactatgaca tgcacgaaat    600
```

| | |
|---|---|
| cattgcccgc ttaaaacgcg ccacgaacg cggcaagaag cacagtatta ttattgttgc | 660 |
| cgaaggtgta ggcagcggtg ttgaattcgg gaaacgcatt gaagaagaaa caaatcttga | 720 |
| aactagggta tctgtattgg gccatatcca gcgcggaggt tctccgagtg ctgctgaccg | 780 |
| tgtgttggca agccgtctcg gcgcatatgc agttgaactg ctgcttgaag gaaaaggcgg | 840 |
| acgctgtgta ggtatacaaa acaataagct tgtagaccat gatattatag aaatacttga | 900 |
| gacaaaacac acagttgagc aaaacatgta tcagctttca aaagaactgt ctatctaatg | 960 |
| tacagctgaa ggctgaagat ttcagaagga agtgaaccaa | 1000 |

<210> SEQ ID NO 4
<211> LENGTH: 1000
<212> TYPE: DNA
<213> ORGANISM: Artificial Sequence
<220> FEATURE:
<223> OTHER INFORMATION: Downstream sequence of pyk locus

<400> SEQUENCE: 4

| | |
|---|---|
| ttacaggtga aaatggaagg ggaatcccct cctttctctc ttatcatgcc ttttgttgaa | 60 |
| cagaacgtgt tacacgtgtg gggggcttgg atatgagatt tttgtttttg cttttattg | 120 |
| tgtttccggc aatagaaatc ggtatattcc tatttttagg aaatctgatt ggtatttgc | 180 |
| cgacagttct attcatgatt ctgactggca ttatcggcgc agcagctgca aaaaaacaag | 240 |
| gaaccgaagt gtattataag gttcagcgtg atcttcaata tggcaaaatg ccgggagaag | 300 |
| cgattgctga cggtctgtgc attttcattg gcggtctatt gctgatgctt ccgggctttt | 360 |
| tatcagattt ggccggcgcc tgtcttctta tcccgtttac ccgcggctgg tgtaagccga | 420 |
| ttctgttcaa atggctgaga ggaatgtcga agaataagcg gatcatcatc aaataaaaaa | 480 |
| cggcagccat gaaaaacgg ctgccgtttt atttttgctg aacggtgata taggaccata | 540 |
| tttcttttaa tgcgcctgtt gtgatgaaag cttggatgat gacgagtaca gccggtcccg | 600 |
| caatcagtcc taaaaacccg aataattaa agccggcaaa cagggcgatg agtgttgcca | 660 |
| gcggatcgat cccgatagat ttacttagta tcttgggctc tgtcagctgc cgctgaataa | 720 |
| gaacgacgag gtacaggata ccaattccga ttgcttgggg cagctggccc gtaatcgata | 780 |
| aatacaaaat ccagggcaca aatacggagc cggcacctaa gtaagggaga agatctacaa | 840 |
| gcccgattaa aaaagcaatt gttgcggcgt gttcaacctt aagagagaa aggccgataa | 900 |
| atacaatcac catcgtgatg aaaacgagga cggcttgtgc tttgataaaa ccagtcattg | 960 |
| cttttttaa ttcgctgctg attgctttgc tgttagctgt | 1000 |

<210> SEQ ID NO 5
<211> LENGTH: 1000
<212> TYPE: DNA
<213> ORGANISM: Artificial Sequence
<220> FEATURE:
<223> OTHER INFORMATION: Upstream sequence of the integration ywkA locus

<400> SEQUENCE: 5

| | |
|---|---|
| gccacccatt ctacactggc cgtcaaaaat tcgcttctgc tgatggtcgt gttgatcgct | 60 |
| ttaacaaaaa atacggtctt aagtaataat agatttctca acaggcaagc agcagtcttg | 120 |
| cctgtttttt atattgtcta aaacacagct ggcagagaga ggggagcgaa gcctatgtac | 180 |
| ataatgaaac aaagcgggtg gcttgagctg atttgcggca gcatgttctc ggggaaatct | 240 |
| gaagagctga tcagaagagt gaagagagca acttatgcca agcaggaagt cagggtattt | 300 |
| aagcctgtaa ttgataaccg atacagcgaa gctgctgttg tctcccataa tggaacatcg | 360 |

```
atgacgagct atgccatttc gtctgctgcg gacatttggg atcacatcag tgaaagtaca    420
gatgtggttg cggttgatga agtgcagttt tttgatcagg aaattgttga ggttttatca    480
tctcttgccg ataaaggcta ccgtgtgata gcagcaggcc ttgatatgga ttttagggga    540
gagccgttcg gtgtcgtccc gaatatcatg gcgattgcgg aaagtgtgac aaagctgcaa    600
gccgtctgtt ctgtttgcgg atcaccggcg agcagaacac agcgcctcat tgacggcaaa    660
cctgcttctt acgatgatcc ggtcattttg gttggtgcag ctgaatcata tgaagcaaga    720
tgcagacatc atcacgaagt cccaggtaaa tctaaaaaat agtccaaaac atgggtataa    780
agatagaatg caccggctaa aaacaccggt gttttttta tattctgata atattcaatt    840
aaaaaattta ataagtata ttaaaaaatt aagtaatttt cttctcttga attttgattt    900
tgacaggcat acaatagctt acgtaatgta aatagttttg agacattgtt cgaataattg    960
tcacaaagtc gcataaagat catgatcggt catatttag                          1000
```

```
<210> SEQ ID NO 6
<211> LENGTH: 1000
<212> TYPE: DNA
<213> ORGANISM: Artificial Sequence
<220> FEATURE:
<223> OTHER INFORMATION: Downstream sequence of ywkA locus

<400> SEQUENCE: 6
ttagcgagta aattttctg tccgagggaa agcttttgt aaagctaaag tatacggaca     60
taggatttgg aggagaatat tttgagcatc ttagatatct taatcctcct ggcgccgatc    120
ttctttgtta tcgtgctggg ttggtttgca ggacattttg gaagttatga tgccaagtcg    180
gcaaaagggg taagtacgtt agtaacgaaa tacgcacttc cagctcactt tatcgctggt    240
attttgacaa cttccagaag tgaatttttta tcacaagtac ctttaatgat ttctttaatt    300
attgggattg ttggtttcta tatcatcatt cttttggttt gcagatttat attcaagtat    360
gatttaacga actcatctgt attttcttg aactctgcac agccgacatt cgcatttatg    420
ggtatcccgg tattgggaag cttattcgga gcgaatgaag ttgcgattcc gatcgcggtc    480
acaggtatcg tggttaacgc gattcttgat ccgctcgcga tcattatcgc tactgttggt    540
gagtcttcta agaaaaacga agagagtggc gacagcttct ggaagatgac aggaaaatca    600
atcctgcatg gtctttgtga gccgcttgca gctgctccgt taatcagtat gatcttggtg    660
ctggttttca atttcactct tcctgagctg gtgttaaaa tgcttgatca gcttggaagc    720
acaacatctg gtgttgctct cttcgctgtt ggtgttaccg ttggtattcg taaaattaaa    780
ctcagtatgc cggctatcgg tattgcgtta ctaaaagttg cggttcagcc tgcgttaatg    840
ttcctgattg ctcttgctat cggacttcca gctgaccaaa caacaaaagc aatccttctt    900
gttgcattcc ctggttctgc cgttgcagcc atgattgcga ctcgtttcga gaaacaagaa    960
gaagaaactg caactgcgtt tgtggtcagt gcgattctgt                         1000
```

```
<210> SEQ ID NO 7
<211> LENGTH: 1000
<212> TYPE: DNA
<213> ORGANISM: Artificial Sequence
<220> FEATURE:
<223> OTHER INFORMATION: Upstream sequence of the integration kdgA locus

<400> SEQUENCE: 7
caactaagag gaggttggga agagatgaag cttgatgcgg tgacattcgg ggaatcaatg     60
```

| | |
|---|---|
| gccatgtttt atgcaaatga gtatggaggc cttcatgaag tatccacttt ttctaaaggg | 120 |
| cttgccggag cagaaagcaa tgtcgcctgc ggccttgcca gactcggatt tcgaatggga | 180 |
| tggatgagca aggtcggcaa tgatcagctc ggaacgttta ttttacaaga gcttaaaaaa | 240 |
| gagggagtgg atgtgtcccg cgtgatccgc tcgcaggacg aaaatcccac cgggctgctg | 300 |
| ctgaagtcaa aagtgaaaga aggcgacccg caagttacct actataggaa aaactcagct | 360 |
| gcaagcacat taactacagc tgaatatccg agagattatt tcaatgcgc aggccatttg | 420 |
| catgtgacag gtattccgcc tgctttatca gccgagatga aagacttcac gtatcatgtc | 480 |
| atgaacgaca tgagaaacgc agggaagacc atttcattcg accctaatgt aagaccttcg | 540 |
| ctttggcctg atcaagcaac aatggtacac acaatcaatg atctggctgg gcttgcagac | 600 |
| tggtttttcc cgggtatcgc agaggggagg ctattgaccg gagaaaaaac acctgaaggc | 660 |
| attgccgact attatttgaa aaaaggtgcc agctttgttg ctattaaaact tggaaaagaa | 720 |
| ggcgcttact ttaaaacggg gacaagtgaa ggatttctag aaggctgccg ggtcgaccgg | 780 |
| gtggttgata cggtcggcgc cggagacgga tttgcagtcg gtgtaatcag cggtatccta | 840 |
| gacggtttgt cgtacaagga tgcggtgcaa aggggaaatg cgattggcgc tttgcaagtg | 900 |
| caggcaccgg gggatatgga cggtttgccg accaggagaa aattagcttc ttttttatct | 960 |
| gctcaaagaa cggttcacca aaagaaaggg gattattaat | 1000 |

<210> SEQ ID NO 8
<211> LENGTH: 1000
<212> TYPE: DNA
<213> ORGANISM: Artificial Sequence
<220> FEATURE:
<223> OTHER INFORMATION: Downstream sequence of kdgA locus

<400> SEQUENCE: 8

| | |
|---|---|
| gtggaattgt tttttcataa ccggaggatg ggagaatcca caatatgaaa atcaaggcga | 60 |
| caattgaacg ggtacctggc ggaatgatga ttattccgct atttcttgga gcggcgctca | 120 |
| acacgtttgc gcctggaaca gcggagttct ttggagggtt tacgggtgct ttgattaccg | 180 |
| gaacgctgcc gatactgggt gttttttatct tttgcgtagg agcaacgatt gattttcgtt | 240 |
| cttcaggcta tatcgcaaga aaaggaatca cgttattatt ggggaagatc ggatttgcgg | 300 |
| cgctgctcgg cgtgatcgca gcgcaattta tacctgacga tggcatacaa tccggctttt | 360 |
| ttgcaggcct ttctgtttta gcaattgtcg cggtaatgaa tgaaacgaac ggcggactgt | 420 |
| atttggcgct catgaatcac atgggaagaa aagaggatgc gggcgctttc gcctttatca | 480 |
| gtacagaatc tggtcctttt atgaccatgg tgacgtttgg tgtgacggga cttgccgcat | 540 |
| tcccatggga aacgctggca gcgacagtca tcccgttttt acttggatgt atacttggaa | 600 |
| atctggatca tgatctcaga gacttattca gcaaggttgt gccggcgatc attccatttt | 660 |
| tcgccttttc gctcggcaat accttgaatt ttggaatgct gatccaatca gggctgctcg | 720 |
| gcatttttat cggagtttct gtcgtcattt tatcgggcag ttctttgttt ttgcttgatc | 780 |
| gttttattgc gcggggagat ggtgtcgcgg gagtggccgc ttcttctacg gcaggggcgg | 840 |
| ctgtagccgt gccatatgca ttagcggaag cgaatgcctc atttgcgcca gttgctgagt | 900 |
| cggcaactgc aattatcgcg acaagcgtta ttgtcacctc gctcttaacc ccgctggcaa | 960 |
| cagtgtgggt agataaaaaa atcaagcaga aaagcggag | 1000 |

<210> SEQ ID NO 9
<211> LENGTH: 1000

```
<212> TYPE: DNA
<213> ORGANISM: Artificial Sequence
<220> FEATURE:
<223> OTHER INFORMATION: Upstream sequence of the integration melA locus

<400> SEQUENCE: 9
acaatccatg tccacgttta tgtatgattt gtatttcaaa cggcaggatg ccggctatgc    60
cgcaacgcaa ggcatattta tggcatttgt cattttgatc atcagctttt gcgcgcttgc   120
gtactttaaa agaaaggaga cggaaatgtc atgagagccg cccgtacaaa aagcatgcgg   180
atcattacgc ttcttgcagc cattgtggcc tgtgcgcatt ttattccttt ttatatcctg   240
ctgaccactt cattgaaagc aaaaggagac tacagttcga atggatatt tccagccgac    300 atctcctttc ataattttc agaggcgtgg gagcgcgctt cgctaggaaa ctcttttata    360
aacaccatga tcatcacagg ttttctgcc ttgttattaa ttatattcgg ctcacttgcc    420
gcctacccgc ttgcccggcg ggaaacgaaa ctgaataaag ccgttttgc cttgctgatt    480 tccattatga tcatccctcc gttaacgtcc atggttcctt tgtaccgaat ggtcgtggac    540
gccggaatgg tcaatacaca cgcaatcgcc attttcatca atacagcggc ttacatgccg    600
ttaaccgtat tcttatattc aggctttatc cgatcgacca ttccaaaaga gcttgtagaa    660
gccgcaagaa ttgacggtgc aggcatgctg aaaatctttt ttacgattgt gtttcctctg    720
ctgaagccga tcactgcgac catctgtatc atttcttgtg tctttatttg aacgactat     780 caatttgcca ttttcttttt acaagatcaa aaggttcaga cattaacagt agccatggca   840
ggttttttcg gagaaaacgc aaacaacctt catttagttg ccgcagcggc acttatggca   900
atgctgccga tggttgttct gttttggcg ctgcaaaaat actttattgc cggcctgtct    960
tccggagcgg taaagggtta acattaaagg gggaagcaat                          1000

<210> SEQ ID NO 10
<211> LENGTH: 1000
<212> TYPE: DNA
<213> ORGANISM: Artificial Sequence
<220> FEATURE:
<223> OTHER INFORMATION: Downstream sequence of melA locus

<400> SEQUENCE: 10
aaactagggg accgctctcc cctagttttt tggttttgtt tcgccttccc aggccatcat    60
gccgccttca acattgactg ttttaaagcc ttgctcatcc aggtacttgc agacgttcat   120
gctgcgcatt cctgagcggc agataaatac gtactctttg tctttatcaa gggtttccat   180
tttttcagga atatccccca tgcgaatatg aacggcttgc gggatcatgc cttccgctac   240
ctcttcatct tctctgacat caattaaata taattcttcg tccgcctcaa tttttttctt   300
caaagcggct gtgctgattt cttttatttc caaagaaaac actcctattc acagtgatca   360
tgttcagtat atcaaagtca gccgaacgat tgctattctg agactgatga aaaaaaatcc    420
ccttttggca aaggggattt tttctaggct tagtttgcca caatattgac aagcttccca    480
ggcaccgcga tgatttccg aatcgttttg ccttcaagct gctctttgac cttttcatct    540
gcttgagcaa gctgttccag ctgttctttc gttgcatcgg caggaacctg taatttcgct    600 tttactttc cgttcagctg aacaacgatt tcaacttcat catccacaag ttttgtttca    660
tcatatacag gccaagcttc gtaggcaatt gtgccggaat ggccaagctt ctcccatagc    720
tcttccgcta agtgtggcgc gacaggagaa agaagcttca cgaagccttc catatattct    780
ttcggcagtt ctgttgcttt ataagcttca ttaataaaga ccatcagctg ggaaataccc    840
```

| gtgttgaaac gaaggccttc ataatggtct gtgactttca tgaccgtttc atgatagacg | 900 |
| cgctccaatg tttcacccgc gccttcaacg attttttccat taagctcacc gctgtcttca | 960 |
| ataaataggc gccatacacg gtcaaggaaa cggcgcgcac | 1000 |

<210> SEQ ID NO 11
<211> LENGTH: 1000
<212> TYPE: DNA
<213> ORGANISM: Artificial Sequence
<220> FEATURE:
<223> OTHER INFORMATION: Upstream sequence of the integration pckA locus

<400> SEQUENCE: 11

| acggacttca cttaggcggc gggctaattt atgggcaagt gaaattggaa gaggcataag | 60 |
| ctctttcgtt tcgttgcacg cataaccgaa cattaatcct tggtcacccg caccaatcgc | 120 |
| ttcaatttct tcgtcgctca ttgtgccttc acgggcttca agcgcttggt ctacgcccat | 180 |
| cgcgatatca gcagactgct catcaattga tgttaaaacc gcacaagttt ccgcatcaaa | 240 |
| tccgtatttt gcacgtgtgt atccgatttc tttaatggtt tggcgaaccg ttttcggaat | 300 |
| gtcaacatac gtagaagttg tgatctctcc gcttacaaga accaaacctg ttgtcacaga | 360 |
| tgtttcacaa gcaacacgcg cgttagggtc tttctttaaa atttcatcta aaatgctgtc | 420 |
| agaaatctgg tcacagattt tatccggatg ccctccgta acagattctg atgtaaataa | 480 |
| acgacgattt ttactcatga tttgcttcct cctgcacaag gcctcccgaa agaccttgta | 540 |
| tatatgatac ggaactcgct ccctcttata caatgtacag ttatattaga gaatgttaat | 600 |
| tggcatattt atgaaataaa aaaacctttt ccatcgagga aagggtttgg tctttgtgcc | 660 |
| tttcactctt atcgctcaag gaatcataca accttgcaac aggttagcac cttggttgtc | 720 |
| tcactcagtt gaacataata aataacagag aaaccggttg ctgggcttca tagggcctgt | 780 |
| ccctccgcca gctcgggata agagtatccg ctcaatgaaa tatcttatcg taaaagggtt | 840 |
| tgcaatgtca atatgattca gaagaaatag gcacctatat tgagggaaaa caatggaaat | 900 |
| gcacacacaa aaaacaataa atagtataga ctatttgaaa atatatgtta tactaattca | 960 |
| caattagcaa aacacaaaaa acgataaagg aaggtttcat | 1000 |

<210> SEQ ID NO 12
<211> LENGTH: 1000
<212> TYPE: DNA
<213> ORGANISM: Artificial Sequence
<220> FEATURE:
<223> OTHER INFORMATION: Upstream sequence of the integration pckA locus

<400> SEQUENCE: 12

| aaaacaaaag ccaagagcaa ttatgctctt ggcttgtttt aattgacgga atgcaaagaa | 60 |
| gtcagcttgt atgtaatgat ggtccggcct tcttcccatt gaagcttctg cacttcagct | 120 |
| gtgcctgact tttcgccaaa ctttgttttg cgtacatcca ttggaatctc catcggatat | 180 |
| actcggtatc cgtccttctc taacgtgaat atattttcat ctatgcgaac ttcttttcct | 240 |
| tttgtcacaa tcagtgtatt aaattcaaca ggcattccca aagtgaaatc cccttttcgtt | 300 |
| ctctttttc tttatcataa catatttcac tgtcagcggt ttttcatcca ttgtgtgagc | 360 |
| tgccgcacga tacgccggtt ttcttttggc gggaaataat gtgtgaatgt actgtagtac | 420 |
| catgttttcca ccggcttatg cagttgtttt agcttctctt ctaataaata ggaatgctga | 480 |
| atcgaaacat tttggtcttt ttctccatgg attaacagca cggagcctg aattttgttt | 540 |
| acttggtcaa acggtgtcct ccattgatat tcctcaggca cctttttcgg tgttccgccg | 600 |

```
atgactcttt tcatcattcg ccgcaaatcc tgccgctcct cgtatgtaag aatcatatca    660
ctgacgcctc cccaggaaac aaatgaagct gcctgcccgc ccatttcgat cgcagtgagc    720
attcccataa ttccgccgcg ggaaaaaccg aagatatgga ttctatcctt cttgacattt    780
gggtgctgct gaagcaggcg aaaagcagaa aatgcatcct ccctgtcttc tccggcaaaa    840
tcctcattgc cttctcctcc ttgattgcct ctgtaaaaag gagcaaacac cacaaaccct    900
tgggatgcaa actggataat ccggcccggc cgaaccatgc ccacgctttt aatcccgccg    960
cgcaaatata aaaatccgtc atattgtccc ggttccgccg                         1000
```

RECOMBINANT STRAIN OF *BACILLUS SUBTILIS*

This application claims priority to Chinese Patent Application No. 201810818899.6, filed on Jul. 24, 2018, which is incorporated by reference for all purposes as if fully set forth herein.

FIELD OF THE INVENTION

The present invention relates to the technical field of genetic engineering, and more particularly to a recombinant strain of *Bacillus subtilis* for promoting acetylglucosamine synthesis of *Bacillus subtilis*.

DESCRIPTION OF THE RELATED ART

In human bodies, acetylglucosamine is a synthetic precursor of a glycosaminoglycan disaccharide unit, which plays an important role in repair and maintenance of cartilage and joint tissue function. Therefore, acetylglucosamine is widely added to medicines and nutritional diets to treat and repair joint damage. In addition, acetylglucosamine also has many applications in the fields of cosmetics and pharmacy. At present, acetylglucosamine is mainly produced by acid hydrolysis of chitin in shrimp shells or crab shells. However, waste liquid produced by the method pollutes the environment seriously, and the resulting products are apt to cause allergic reactions, being not suitable for people who are allergic to seafood.

*Bacillus subtilis* is widely used as a production host for food enzymic preparations and vital nutrient chemicals, and its products are certified as the Generally Regarded as Safe (GRAS) security level by FDA. The reaction formula for producing acetylglucosamine by fermentation of *Bacillus subtilis* is:

$$5/2\,glucose + ATP + 5NAD^+ + 2NH_3 \rightarrow GlcNAc + glutamate + ADP + 5NADH + 2CO_2 + phosphate$$

The formula is obtained by calculating three precursors, namely 6-phosphate fructoses, acetyl coenzyme A and glutamine, of the de novo synthesis of acetylglucosamine, it can be seen from the formula that a large amount of NADH would be generated in the synthesis process of acetylglucosamine. The excessively generated NADH has a huge negative effect on the maximum theoretical yield (Yc) of the N-acetylglucosamine pathway. Due to the fact that cells need to maintain the balance of reduction force, the excessively generated NADH will be consumed in two ways: participating in the synthesis of other metabolites (resulting in the generation of by-products), and the other aspect being oxidized to produce ATP (causing a large amount of $O_2$ to be consumed during the fermentation process, and meanwhile, a large amount of bacterial cells is greatly produced). In addition, the use of *Bacillus subtilis* to synthesize acetylglucosamine is accompanied by metabolic overflow, resulting in the massive synthesis of by-product acetoin. Therefore, effectively treating the NADH concomitantly generated with the acetylglucosamine and the synthesis efficiency of the acetylglucosamine, meanwhile, avoiding the overflow of central carbon metabolism and improving the economical efficiency of carbon atoms, are urgent problems to be solved in the production of acetylglucosamine by the method of microbial fermentation.

SUMMARY OF THE INVENTION

To solve the above technical problems, the present invention provides a recombinant strain for improving acetylglucosamine synthesis of *Bacillus subtilis*. The recombinant strain of the invention can eliminate central carbon metabolism overflow, balance intracellular reducing force and promote acetylglucosamine synthesis greatly.

To achieve the above purpose, the present invention utilizes the following technical solutions.

In one aspect, the invention provides a recombinant strain of *Bacillus subtilis*, and pyruvate carboxylase BalpycA, glyceraldehyde-3-phosphate ferredoxin dehydrogenase gor, isocitrate $NAD^+$ dehydrogenase icd, malate quinone dehydrogenase mqo, pyruvate ferredoxin oxidoreductase porAB and nitrogenase ferritin cyh are integrated and expressed in the recombinant strain.

In one embodiment of the invention, the recombinant strain is obtained by using *Bacillus subtilis* BSGNKAP2 as a starting strain. The *Bacillus subtilis* BSGNKAP2 is disclosed in the patent application No. CN 201610517961.9.

In a preferable embodiment of the invention, the pyruvate carboxylase BalpycA, glyceraldehyde-3-phosphate ferredoxin dehydrogenase gor, isocitrate $NAD^+$ dehydrogenase icd, malate quinone dehydrogenase mqo, pyruvate ferredoxin oxidoreductase porAB and nitrogenase ferritin cyh are respectively expressed by using a strong constitutive promoter.

In a more preferable embodiment, the strong constitutive promoter is a promoter suitable for *Bacillus subtilis* such as $P_{43}$, $P_{abrB}$, $P_{valS}$, $P_{hag}$, $P_{spovG}$, $P_{yvyD}$, $P_{hemA}$ or $P_{ffh}$ promoter. Preferably, the strong constitutive promoter is $P_{43}$ promoter.

In a specific embodiment of the invention, the encoding gene balpycA of the pyruvate carboxylase BalpycA is shown as NCBI-Protein ID: AAS42897, and the encoding gene balpycA of the pyruvate carboxylase BalpycA can be integrated into malS, pyk, ywkA, kdgA, melA, pckA, ctc, yckB, ydgG, speA, bshB, yojF, brxA, yqhS, yqeT, recJ, yvmB, spSC or rrnO locus in *Bacillus subtilis* genome. Preferably, the encoding gene balpycA is integrated into malS locus in *Bacillus subtilis* genome.

In another specific embodiment of the invention, the encoding gene gor of glyceraldehyde-3-phosphate ferredoxin dehydrogenase is shown as NCBI-Protein ID: CAF30501, and the encoding gene gor can be integrated into pyk, malS, ywkA, kdgA, melA, pckA, ctc, yckB, ydgG, speA, bshB, yojF, brxA, yqhS, yqeT, recJ, yvmB, spSC, nupG or rrnO locus in *Bacillus subtilis* genome. Preferably, the encoding gene gor of glyceraldehyde-3-phosphate ferredoxin dehydrogenase is integrated into pyk locus in *Bacillus subtilis* genome.

In still another embodiment of the invention, the encoding gene icd of the isocitrate $NAD^+$ dehydrogenase is shown as NCBI-Protein ID: AKC61181, and the encoding gene icd can be integrated into ywkA, pyk, malS, kdgA, melA, pckA, ctc, yckB, ydgG, speA, bshB, yojF, brxA, yqhS, yqeT, recJ, yvmB, spSC, nupG or rrnO locus in *Bacillus subtilis* genome. Preferably, the encoding gene icd of the isocitrate $NAD^+$ dehydrogenase is integrated into ywkA locus in *Bacillus subtilis* genome.

In a specific embodiment of the invention, the encoding gene mqo of the malate quinone dehydrogenase is shown as NCBI-Protein ID: ADK05552, and the encoding gene mqo can be integrated into kdgA, pyk, ywkA, malS, melA, pckA, ctc, yckB, ydgG, speA, bshB, yojF, brxA, yqhS, yqeT, recJ, yvmB, spSC, nupG or rrnO in *Bacillus subtilis* genome. Preferably, the encoding gene mqo of the malate quinone dehydrogenase is integrated into kdgA locus in *Bacillus subtilis* genome.

In another specific embodiment of the invention, the encoding genes porAB of the pyruvate ferredoxin oxidoreductase are shown as NCBI-Protein ID: ADK06337 and NCBI-Protein ID: ADK06336, and the encoding genes porAB can be integrated into melA, pyk, ywkA, kdgA, malS, pckA, ctc, yckB, ydgG, speA, bshB, yojF, brxA, yqhS, yqeT, recJ, yvmB, spSC, nupG or rrnO locus in *Bacillus subtilis* genome. Preferably, the encoding genes porAB of the pyruvate ferredoxin oxidoreductase are integrated into melA locus in *Bacillus subtilis* genome.

In a specific embodiment of the invention, the encoding gene cyh of the nitrogenase ferritin is shown as NCBI-Protein ID: ACV00712, and the encoding gene cyh can be integrated into pckA, pyk, ywkA, kdgA, melA, malS, ctc, yckB, ydgG, speA, bshB, yojF, brxA, yqhS, yqeT, recJ, yvmB, spSC, nupG or rrnO locus in *Bacillus subtilis* genome. Preferably, the encoding gene cyh of the nitrogenase ferritin is integrated into pckA locus in *Bacillus subtilis* genome.

In one embodiment of the present invention, the encoding gene balpycA of pyruvate carboxylase BalpycA is derived from *Bacillus cereus*. The exogenously introduced pyruvate carboxylase BalpycA derived from. *Bacillus cereus* can eliminate the central carbon metabolism overflow of the *Bacillus subtilis* and avoid the synthesis of the by-product acetoin.

In one embodiment of the present invention, the encoding gene gor of the glyceraldehyde-3-phosphate ferredoxin dehdrogenase is derived from *Methanococcus maripaludis* KA1.

In one embodiment of the present invention, the encoding gene icd of the isocitrate NAD$^+$ dehydrogenase is derived from *Clostridium sporogenes*.

In one embodiment of the present invention, the encoding gene mqo of the malate quinone dehydrogenase is derived from *Bacillus cereus*.

In one embodiment of the present invention, the encoding gene porAB of the pyruvate ferredoxin oxidoreductase is derived from *Bacillus cereus*.

In one embodiment of the present invention, the encoding gene cyh of the nitrogenase ferritin is derived from *Cyanothece* sp. PCC 8802.

In the invention, five exogenous reducing force metabolic reactions are introduced to replace the reaction of generating NADH in glycolysis pathway and tricarboxylic acid cycle to reconstruct intracellular reducing force metabolism, and they specifically comprise glyceraldehyde-3-phosphate ferredoxin dehydrogenase gor, isocitrate NAD$^+$ dehydrogenase icd, a malate quinone dehydrogenase mqo, a ketoacid ferredoxin oxidoreductase porAB and a nitrogenase ferritin cyh. The operation is simple and convenient to use. And in the reconstructed recombinant strain of *Bacillus subtilis*, the central carbon metabolism overflow is avoided and the intracellular reducing force metabolism is balanced.

In another aspect, the present invention also provides a method for constructing the recombinant strain of *Bacillus subtilis*, and the method includes the following steps:

(1) constructing respectively homologous recombination integration cassettes of the pyruvate carboxylase BalpycA encoding gene balpycA, the glyceraldehyde-3-phosphate ferredoxin dehydrogenase encoding gene gor, the isocitrate NAD$^+$ dehydrogenase encoding gene icd, the malate quinone dehydrogenase encoding gene mqo, the pyruvate ferredoxin oxidoreductase encoding gene porAB, and the nitrogenase ferritin encoding gene cyh; and (2) integrating the integration cassettes obtained in the step (1) into the *Bacillus subtilis* genome respectively by homologous recombination.

In one embodiment of the invention, in the step (1), upstream sequence (500-1000 bp) of the integration locus, zeocin resistant gene zeo sequence and strong constitutive promoter, target gene sequence and downstream sequence (500-1000 bp) are used for constructing an integration cassette.

In a preferable embodiment, the target gene sequence is selected from the group consisting of the pyruvate carboxylase BalpycA encoding gene balpycA, the glyceraldehyde-3-phosphate ferredoxin dehydrogenase encoding gene gor, the isocitrate NAD$^+$ dehydrogenase encoding gene icd, the malate quinone dehydrogenase encoding gene mqo, the pyruvate ferredoxin oxidoreductase encoding gene porAB, and the nitrogenase ferritin encoding gene cyh.

In still another aspect, the invention also provides use of the recombinant strain in fermentation production of acetylglucosamine.

Preferably, the use employs the following steps: activating the recombinant strain in a seed medium, then transferring activated seeds into a fermentation medium, adding an inducer to carry out fermentation culture to obtain acetylglucosamine.

In one embodiment of the present invention, seeds are activated in the seed medium at a temperature of 35-38° C., and activated seeds are fermented and cultured at a temperature of 35-38° C.

In one embodiment of the present invention, the seed medium includes the following ingredients: peptone, yeast powder and sodium chloride.

In one specific embodiment of the invention, the seed medium includes the following ingredients by weight: 5-15 g/L of peptone, 5-10 g/L of yeast powder and 5-15 g/L of sodium chloride.

In one embodiment of the invention, the fermentation medium includes the following ingredients: glucose, peptone, yeast powder, ammonium sulfate, dipotassium hydrogen phosphate, potassium dihydrogen phosphate, calcium carbonate, and a trace element solution.

In one specific embodiment of the invention, the fermentation medium includes the following ingredients by weight: 15-25 g/L of glucose, 5-8 g/L of peptone, 10-15 g/L of yeast powder, 5-8 g/L of ammonium sulfate, 10-15 g/L of dipotassium hydrogen phosphate, 2-3 g/L of potassium dihydrogen phosphate, 4-6 g/L of calcium carbonate, and 8-12 ml/L of trace element solution.

In one embodiment of the present invention, the trace element solution includes: manganese sulfate, cobalt chloride, sodium molybdate, zinc sulfate, aluminum chloride, copper chloride, boric acid and hydrochloric acid.

In a preferable embodiment of the present invention, the trace element solution includes the following ingredients by weight: 0.8-1.2 g/L of manganese sulfate, 0.2-0.6 g/L of cobalt chloride, 0.1-0.3 g/L of sodium molybdate, 0.1-0.3 g/L of zinc sulfate, 0.1-0.3 g/L of aluminum chloride, 0.1-0.3 g/L of copper chloride, 0.04-0.06 g/L of boric acid, and 3-8 mol/L of hydrochloric acid.

In one embodiment of the present invention, the activated seeds are transferred to the fermentation medium at an inoculum size of 5-15% for culture.

In a preferable embodiment of the present invention, the inducer is xylose, and the dosage of xylose for fermentation medium is 5-10 g per liter.

By means of the above technical solutions, as compared with the prior art, the invention has the following advantages:

The present invention provides a method for eliminating central carbon metabolism overflow of *Bacillus subtilis*, balancing intracellular reducing force, and promoting acetylglucosamine synthesis. Pyruvate carboxylase BalpycA is exogenously introduced from *Bacillus cereus*, thus eliminating the central carbon metabolism overflow of the *Bacillus subtilis* and avoiding the synthesis of the by-product acetoin. Further, five exogenous reducing force metabolic reactions are introduced to replace the reaction of generating NADH in glycolysis pathway and tricarboxylic acid cycle to reconstruct intracellular reducing force metabolism, they specifically comprise glyceraldehyde-3-phosphate ferredoxin dehydrogenase, isocitrate $NAD^+$ dehydrogenase, a malate quinone dehydrogenase, a ketoacid ferredoxin oxidoreductase and a nitrogenase ferritin. As compared with the starting strain BSGNKAP2, the central carbon metabolism overflow is avoided and the synthesis of by-product acetoin is eliminated. Furthermore, in the process of producing acetylglucosamine, the intracellular NADH is effectively reduced, and the acetylglucosamine synthesis is promoted. In a shake-flask fermentation process using a complex medium, acetylglucosamine yield of the recombinant strain is 24.50 g/L, acetylglucosamine/glucose yield is 0.469 g/g, respectively 1.97 times and 2.13 times of those of the starting strain BSGNKAP2. The construction method of recombinant *Bacillus subtilis* of the invention is simple and is convenient to use, and has a good application prospect.

DETAILED DESCRIPTION OF THE PREFERRED EMBODIMENTS

The technical solutions in the embodiments of the present invention will be described clearly and completely in combination with the accompanying drawings. Obviously, the described embodiments are parts of the embodiments of the present invention, instead of all of the embodiments. On the basis of the embodiments in the present invention, all other embodiments obtained by those skilled in the art without creative work belong to the protection scope of the present invention.

Embodiment 1

Construction of *Bacillus subtilis* BSGNKAP3

The *Bacillus subtilis* BSGNKAP2 was *B. subtilis* 168ΔnagPΔgamPΔgamAΔnagA4nagBΔldhΔptaΔglcK ΔpckA Δpyk $P_{43}$-glmS P43-pycA::lox72, and GNA1 gene was freely expressed by using pP43NMK-GNA1 plasmid. The specific construction method can be referred to the disclosure of Patent Application CN 201610517961.9. Then, based on this, the pyruvate carboxylase BalpycA encoding gene balpycA (NCBI-Protein ID: AAS42897) derived from *Bacillus cereus* was integrated into malS locus in *Bacillus subtilis* BSGNKAP2 genome. Upstream sequence (SEQ ID No. 1, 1000 bp) of the integration malS locus, zeocin resistant gene zeo sequence, strong constitutive promoter $P_{43}$, target gene sequence balpycA and downstream sequence (SEQ ID No. 2, 1000 bp) of malS locus were used for constructing an integration cassette. The integration cassettes obtained were integrated into the *Bacillus subtilis* BSGNKAP2 genome by homologous recombination. By screening through zeocin resistance flat plates, carrying out colony PCR verification and sequencing, it was confirmed that integration was successful and the recombinant *Bacillus subtilis* BSGNKAP3 was obtained.

Embodiment 2

Construction of *Bacillus subtilis* BSGNKAP4

*Bacillus subtilis* BSGNKAP3 was used as the host, and GNA1 gene was freely expressed by using pP43NMK-GNA1 plasmid. The glyceraldehyde-3-phosphate ferredoxin dehydrogenase encoding gene gor (NCBI-ProteinID: CAF30501) was integrated into pyk locus in *Bacillus subtilis* BSGNKAP3 genome. Upstream sequence (SEQ ID No. 3, 1000 bp) of the integration pyk locus, zeocin resistant gene zeo sequence, strong constitutive promoter $P_{43}$, target gene sequence gor and downstream sequence (SEQ ID No. 4, 1000 bp) of pyk locus were used for constructing an integration cassette. The obtained integration cassette was integrated into the *Bacillus subtilis* BSGNKAP3 genome by homologous recombination. By screening through zeocin resistance flat plates, carrying out colony PCR verification and sequencing, it was confirmed that integration was successful and the recombinant *Bacillus subtilis* BSGNKAP4 was obtained.

Embodiment 3

Construction of Recombinant *Bacillus subtilis* BSGNKAP5

BSGNKAP4 was used as the host, and GNA1 gene was freely expressed by using pP43NMK-GNA1 plasmid. The isocitrate $NAD^+$ dehydrogenase encoding gene icd (NCBI-Protein ID: AKC61181) was integrated into ywkA locus in *Bacillus subtilis* BSGNKAP4 genome. Upstream sequence (SEQ ID No. 5, 1000 bp) of the integration ywkA locus, zeocin resistant gene zeo sequence, strong constitutive promoter $P_{43}$, target gene sequence icd and downstream sequence (SEQ ID No. 6, 1000 bp) of ywkA locus were used for constructing an integration cassette. The obtained integration cassette was integrated into the *Bacillus subtilis* BSGNKAP4 genome by homologous recombination. By screening through zeocin resistance flat plates, carrying out colony PCR verification and sequencing, it was confirmed that integration was successful and the recombinant *Bacillus subtilis* BSGNKAP5 was obtained.

Embodiment 4

Construction of Recombinant *Bacillus subtilis* BSGNKAP6

BSGNKAP5 was used as the host, and GNA1 gene was freely expressed by using pP43NMK-GNA1 plasmid. The malate quinone dehydrogenase encoding gene mqo (NCBI-Protein ID: ADK05552) was integrated into kdgA locus in *Bacillus subtilis* BSGNKAP5 genome. Upstream sequence (SEQ ID No. 7, 1000 bp) of the integration kdgA locus, zeocin resistant gene zeo sequence, strong constitutive promoter $P_{43}$, target gene sequence mqo and downstream sequence (SEQ ID No. 8, 1000 bp) of kdgA locus were used for constructing an integration cassette. The obtained integration cassette was integrated into the *Bacillus subtilis* BSGNKAP5 genome by homologous recombination. By screening through zeocin resistance flat plates, carrying out colony PCR verification, it was confirmed that integration was successful and the recombinant *Bacillus subtilis* BSGNKAP6 was obtained.

Embodiment 5

Construction of Recombinant *Bacillus subtilis* BSGNKAP7

BSGNKAP6 was used as the host, and GNA1 gene was freely expressed by using pP43NMK-GNA1 plasmid. The pyruvate ferredoxin oxidoreductase encoding genes porAB (NCBI-Protein ID: ADK06337 and NCBI-Protein ID: ADK06336) were integrated into melA locus in *Bacillus subtilis* BSGNKAP6 genome. Upstream sequence (SEQ ID No. 9, 1000 bp) of the integration melA locus, zeocin resistant gene zeo sequence, strong constitutive promoter $P_{43}$, target gene sequence porAB and downstream sequence (SEQ ID No. 10, 1000 bp) of melA locus were used for constructing an integration cassette. The obtained integration cassette was integrated into the *Bacillus subtilis* BSGNKAP6 genome by homologous recombination. By screening through zeocin resistance flat plates, carrying out colony PCR verification and sequencing, it was confirmed that integration was successful and the recombinant *Bacillus subtilis* BSGNKAP7 was obtained.

Embodiment 6

Construction of *Bacillus subtilis* BSGNKAP8

BSGNKAP7 was used as the host, and GNA1 gene was freely expressed by using pP43NMK-GNA1 plasmid. The nitrogenase ferritin encoding gene cyh (NCBI-Protein ID: ACV00712) was integrated into pckA locus in *Bacillus subtilis* BSGNKAP7 genome. Upstream sequence (SEQ ID No. 11, 1000 bp) of the integration pckA locus, zeocin resistant gene zeo sequence, strong constitutive promoter $P_{43}$, target gene sequence cyh and downstream sequence (SEQ ID No. 12, 1000 bp) of pckA locus were used for constructing an integration cassette. The obtained integration cassette was integrated into the *Bacillus subtilis* BSGNKAP7 genome by homologous recombination. By screening through zeocin resistance flat plates, carrying out colony PCR verification and sequencing, it was confirmed that integration was successful and the recombinant *Bacillus subtilis* BSGNKAP7 was obtained.

In the above embodiments of the invention, besides the promoter $P_{43}$, other promoters suitable for *Bacillus subtilis* can also be used, such as, $P_{abrB}$, $P_{valS}$, $P_{hag}$, $P_{spoVG}$, $P_{yvyD}$, $P_{hemA}$ or $P_{fjh}$.

The pyruvate carboxylase BalpycA encoding gene balpycA also can be integrated into other loci in *Bacillus subtilis* genome, such as, pyk, ywkA, kdgA, melA, pckA, ctc, yckB, ydgG, speA, bshB, yojF, brxA, yqhS, yqeT, recJ, yvmB, spSC, nupG or rrnO locus.

The glyceraldehyde-3-phosphate ferredoxin dehydrogenase encoding gene gor also can be integrated into other loci in *Bacillus subtilis* genome, such as, malS, ywkA, kdgA, melA, pckA, ctc, yckB, ydgG, speA, bshB, yojF, brxA, yqhS, yqeT, recJ, yvmB, spSC, nupG or rrnO locus.

The isocitrate $NAD^+$ dehydrogenase encoding gene icd also can be integrated into other loci in *Bacillus subtilis* genome, such as, pyk, malS, kdgA, melA, ctc, yckB, ydgG, speA, bshB, yojF, brxA, yqhS, yqeT, recJ, yvmB, spSC, nupG or rrnO locus.

The malate quinone dehydrogenase encoding gene mqo also can be integrated into other loci in *Bacillus subtilis* genome, such as, pyk, ywkA, malS, melA, pckA, ctc, yckB, ydgG, speA, bshB, yojF, brxA, yqhS, yqeT, recJ, yvmB, spSC, nupG or rrnO locus.

The pyruvate ferredoxin oxidoreductase encoding genes porAB also can be integrated into other loci in *Bacillus subtilis* genome, such as, pyk, ywkA, kdgA, malS, pckA, ctc, yckB, ydgG, speA, bshB, yojF, brxA, yqhS, yqeT, recJ, yvmB, spSC, nupG or rrnO locus.

The nitrogenase ferritin encoding gene cyh also can be integrated into other loci in *Bacillus subtilis* genome, such as, pyk, ywkA, kdgA, melA, malS, ctc, yckB, ydgG, speA, bshB, yojF, brxA, yqhS, yqeT, recJ, yvmB, spSC, nupG or rrnO locus.

Embodiment 7

Production of Acetylglucosamine by Fermenting Recombinant *Bacillus subtilis*

The ingredients of the seed medium included: 10 g/L of peptone, 5 g/L of yeast powder, and 10 g/L of sodium chloride.

The ingredients of the fermentation medium included: 20 g/L of glucose, 6 g/L of peptone, 12 g/L of yeast powder, 6 g/L of ammonium sulfate, 12.5 g/L of dipotassium hydrogen phosphate, 2.5 g/L of potassium dihydrogen phosphate, 5 g/L of calcium carbonate, and 10 ml/L of trace element solution.

The trace element solution included the following ingredients by weight: 1.0 g/L of manganese sulfate, 0.4 g/L of cobalt chloride, 0.2 g/L of sodium molybdate, 0.2 g/L of zinc sulfate, 0.1 g/L of aluminium chloride, 0.1 g/L of copper chloride, 0.05 g/L of boric acid, and 5 mol/L of hydrochloric acid.

High performance liquid chromatography (HPLC) was used for detecting content of acetylglucosamine. HPLC test conditions were as follows: instrument model: Agilent 1200, RID detector, column: $NH_2$ column (250×4.6 mm, 5 μm); mobile phase: 70% acetonitrile, flow rate: 0.75 mL/min; column temperature: 30° C., and injection volume: 10 μL.

Detection of Glucose Concentration in Fermentation Broth: SBA Biosensor Analyzer.

Recombinant *Bacillus subtilis* BSGNKAP8 was cultured under 37° C. at 220 rpm for 8 h in the seed medium, and then seeds were transferred to the fermentation medium at the inoculum size of 5% and cultured under 37° C. at 220 rpm for 48 h in a 500 ml shake flask. At the end of the fermentation, the content of acetylglucosamine in the fermentation supernatant was measured.

Figure 1:
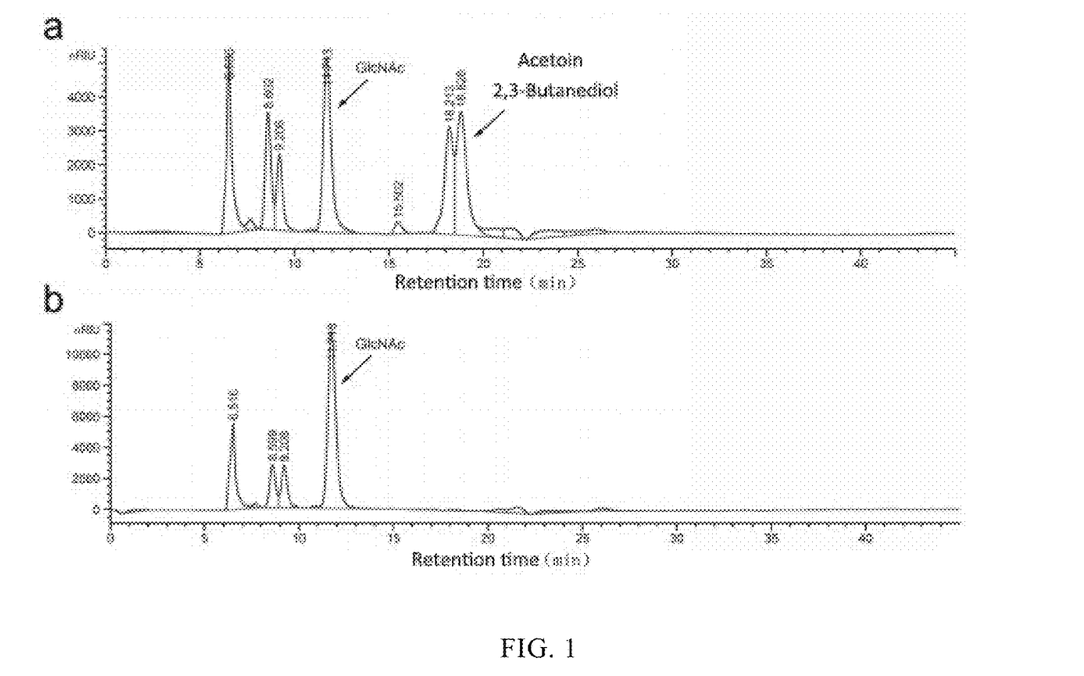
FIG. 1 is a high performance liquid chromatography (HPLC) differential detection chromatograph for producing acetylglucosamine by fermenting *Bacillus subtilis*, in which, (a) shows HPLC detection results of BSGNKAP2 fermentation broth, and (b) shows HPLC detection results of BSGNKAP3 fermentation broth.

After shake-flask fermentation was completed, the acetyglucosamine yield of BSGNKAP8 was 24.50 g/L, and the acetyglucosamine/glucose yield was 0.469 g/g, respectively 1.97 times and 2.13 times of those of the starting strain BSGNKAP2 (as shown in FIG. 1). Thus, in the invention, increase of the extracellular production of acetylglucosamine in the recombinant *Bacillus subtilis* is achieved. In addition, acetoin is completely eliminated (as shown in FIG. 1).

TABLE 1

Comparison of acetylglucosamine and acetylglucosamine/glucose

| Strain | BSGNK AP2 | BSGNK AP3 | BSGNK AP4 | BSGNK AP5 | BSGNK AP6 | BSGNK AP7 | BSGNK AP8 |
|---|---|---|---|---|---|---|---|
| Acetaminoglucose (g/L) | 12.4 ± 0.56 | 14.3 ± 0.28 | 17.5 ± 0.86 | 19.7 ± 1.11 | 18.1 ± 0.75 | 21.5 ± 0.44 | 24.5 ± 0.68 |
| Acetylglucosamine/ glucose (g/g) | 0.22 ± 0.01 | 0.33 ± 0.01 | 0.35 ± 0.02 | 0.40 ± 0.02 | 0.42 ± 0.02 | 0.39 ± 0.01 | 0.47 ± 0.01 |

Embodiment 8

Detection of Intracellular NADH of Recombinant *Bacillus subtilis*

The detection of intracellular NADH was performed by using the kits from Qingdao Jieshikang Biotechnology Co., Ltd. The thalluses in the logarithmic growth period were collected into centrifuge tubes ($10^4$), alkaline extract was added at the volume ratio of 500-1000:1. Ultrasonic crushing was performed (ice bath, 20% or 200 W power, ultrasonic for 3 s, interval for 10 s, repeated for 30 times), water bath was carried out at 95° C. for 5 min (tightened to prevent water loss), and after cooling in ice bath, 10000 g of the resulting solution was centrifuged at 4° C. for 10 min, then 500 uL acidic extract was added to 500 uL supernatant for neutralizing, after uniformly mixing, centrifuging was performed on 10000 g of solution at 4° C. for 10 min, the supernatant was taken and placed on the ice to detect NADH according to the standard kit procedures.

Figure 2:
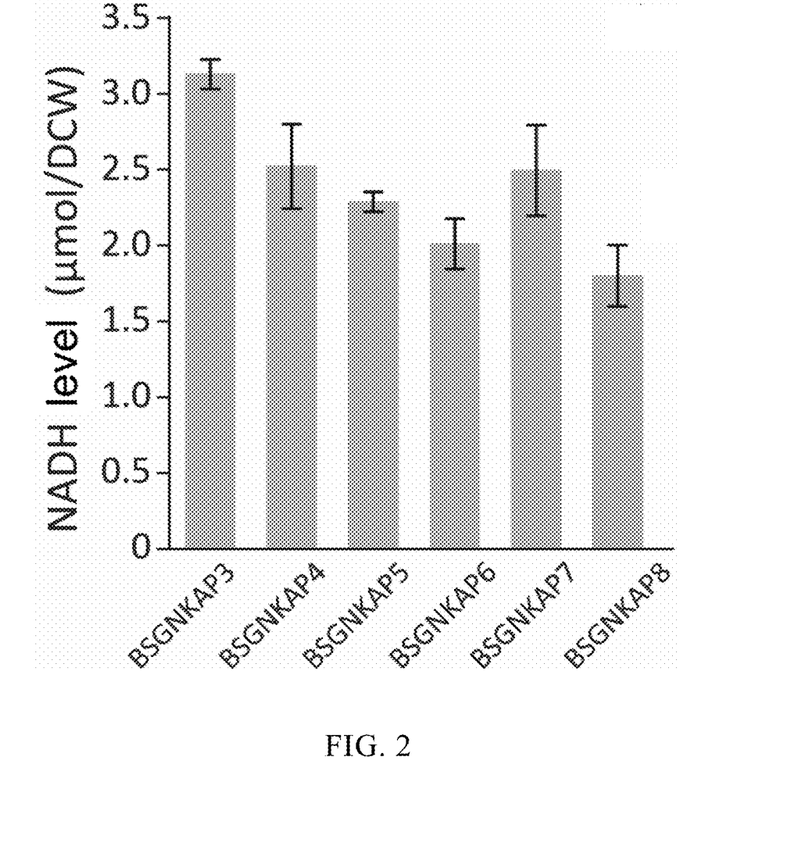
FIG. 2 shows the intracellular NADH levels of *Bacillus subtilis* engineered strains.

Intracellular NADH levels of BSGNKAP3, BSGNKAP4, BSGNKAP5, BSGNKAP6, BSGNKAP7 and BSGNKAP8 are shown in FIG. 2. It shows that the *Bacillus subtilis* of the invention can completely avoid central carbon metabolism overflow, effectively avoid accumulation of intracellular reducing force NADH, and promote the synthesis of acetyl-glucosamine.

The abovementioned description of the disclosed embodiments enables those skilled in the art to implement or use the present invention. Multiple modifications to these embodiments are obvious to those skilled in the art, and general principles defined herein can be implemented in other embodiments without departing from the spirit or scope of the present invention. Therefore, the present invention will not be limited to theses embodiments illustrated herein, but needs to be in line with the widest scope consistent with the principles and novel features disclosed herein.

What is claimed is:

1. A recombinant strain of *Bacillus subtilis*, wherein pyruvate carboxylase BalpycA, glyceraldehyde-3-phosphate ferredoxin dehydrogenase gor, isocitrate $NAD^+$ dehydrogenase icd, malate quinone dehydrogenase mqo, pyruvate ferredoxin oxidoreductase porAB and nitrogenase ferritin cyh are integrated and expressed in the recombinant strain, wherein the pyruvate carboxylase BalpycA, glyceraldehyde-3-phosphate ferredoxin dehydrogenase gor, isocitrate $NAD^+$ dehydrogenase icd, malate quinone dehydrogenase mqo, pyruvate ferredoxin oxidoreductase porAB and nitrogenase ferritin cyh are respectively expressed by using a strong constitutive promoter.

2. The recombinant strain according to claim 1, wherein the strong constitutive promoter is $P_{43}$, $P_{abrB}$, $P_{valS}$, $P_{hag}$, $P_{spoVG}$, $P_{yvyD}$, $P_{hemA}$ or $P_{ffh}$ promoter.

* * * * *